Nov. 24, 1970 P. DICKSON Plant Pat. 3,006
ROSE PLANT
Filed Jan. 28, 1969
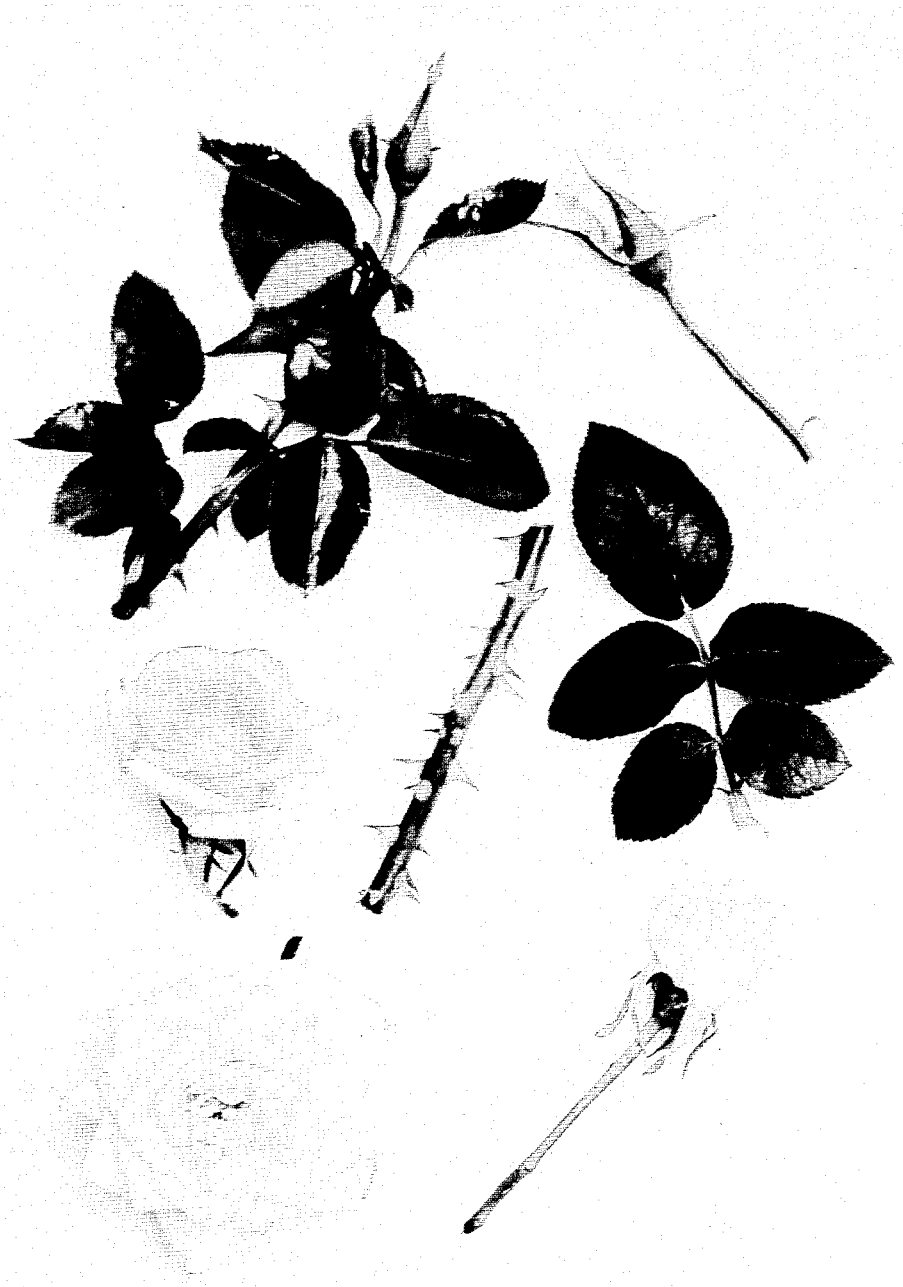
Inventor.
Patrick Dickson
By: Robb & Robb
Attorneys.

United States Patent Office

Plant Pat. 3,006
Patented Nov. 24, 1970

3,006
ROSE PLANT

Patrick Dickson, Newtownards, Ireland, assignor to Jackson & Perkins Company, Newark, N.Y., a corporation of New York Filed Jan. 28, 1969, Ser. No. 794,810
Int. Cl. A01h 5/00
U.S. Cl. Plt.—22 1 Claim The present invention relates to a new and distinct variety of rose plant of the floribunda class, which was originated by me by crossing an unnamed and unpatented seedling of the parentage consisting of an unnamed and unpatented seedling of ["Karl Herbst" (unpatented) × "Masquerade" (U.S. Plant Pat. No. 975] × "Faust" (unpatented), with the variety "Piccadilly" (unpatented).

The primary objective of this breeding was to produce a new and improved rose variety of the floribunda class which bears long-lasting yellow flowers. This objective was fully achieved, along with other desirable features, as evidenced by the following unique combination of characteristics which are outstanding in the new variety and which distinguish it from its parents, as well as from all other varieties of which I am aware:

(1) A vigorous and well-branched plant habit attaining an average height of about 2½ feet;

(2) Flowers of medium size and which are borne both singly and in small clusters; and (3) A distinctive and attractive Saffron Yellow flower color which is overcast distinctively on the petal tips with Brick Red.

Asexual reproduction of my new rose variety by budding, as performed at Newark, N.Y., U.S.A., and also at Livermore, Calif., U.S.A., shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (1941), except where general color terms of ordinary dictionary significance are obvious:

Parentage: Seedling.
- *Seed parent.*—An unnamed seedling derived from ("Karl Herbst" × "Masquerade") × "Faust."
- *Pollen parent.*—"Piccadilly."

Classification:
- *Botanical.*—Rosa.
- *Commercial.*—Floribunda.

Propagation: Holds its distinguishing characteristics through succeeding propagations by budding.

FLOWER (Observations made from specimens grown at Newark, N.Y., U.S.A. in the afternoon during the middle of the month of September.)

Blooming habit:
- *Recurrent.*—Continuous.

Bud:
- *Size.*—Small.
- *Form.*—Pointed.
- *Color.*—As sepals first divide: Chrome Yellow, Plate 605/1. Petal area exposed between sepals before sepals unfold: Garnet Brown, Plate 00918/3. When half-blown: Inside of petals—Saffron Yellow, Plate 7/1, heavily overlaid with Brick Red, Plate 016; reverse of petals—Saffron Yellow, Plate 7/1.

- *Sepals.*—Smooth edge; slight serrated point. Color: Outside lighter than Spinach Green, Plate 0960, partly overcast with Garnet Brown, Plate 00918/3.
- Receptacle.—Color: Spinach Green, Plate 0960. Shape: Apple. Size: Large. Surface: Smooth.
- *Peduncle.*—Length: Long. Surface: Prickly. Color: Bronze.
- *Opening.*—Spiral petals recurring on outer edges only.

Bloom:
- *Size.*—Medium.
- *Borne.*—Both singly and several together.
- *Stems.*—Medium length; strong.
- *Form.*—*High-centered; retains its form to the end.*
- *Petalage.*—Number of petals under normal conditions: 25.
- *Color.*—Center of flower: Saffron Yellow, plate 7/1, overcast lightly with Brick Red, Plate 016. Outer petals: Saffron Yellow, Plate 7/1, slightly shaded on petal edges with Brick Red, Plate 016. Reverse of petals: From Saffron Yellow, Plate 7/3 to Saffron Yellow, Plate 7/2. Base of petals: Same as reverse. General tonality from a distance: From Saffron Yellow, Plate 7 to Saffron Yellow, Plate 7/3, with shading of Brick Red, Plate 016.
- *Discoloration.*—Color fades only slightly from foregoing description by end of third day.

Petals:
- *Texture.*—Thick.
- *Surface.*—Shiny.
- *Form.*—Round.
- *Arrangement.*—Imbricated.
- *Petaloids in center.*—Few.
- *Persistance.*—Drop off cleanly.
- *Fragrance.*—Slight.
- *Lasting quality.*—On the plant: Very long. As cut flower: Very long.

REPRODUCTIVE ORGANS

Anthers: Medium size; many.
- *Color.*—Yellow.

Filaments (threads): Medium length.

Pollen:
- *Color.*—Lemon yellow.

Styles: Loosely separated; uneven length.

Stigmas:
- *Color.*—Light yellow.

Hips: None observed.

Seeds: None observed.

PLANT

Form: Bush:

Growth: Vigorous; well-branched; attains average height of about 2½ feet.

Foliage: Compound of 5 leaflets.
- *Size.*—Medium.
- *Quantity.*—Abundant.
- *Color.*—New foliage (upper surface): Normal green and bronzy. Old foliage (upper surface): Dark green.
- *Shape.*—Oval; bluntly pointed.
- *Texture.*—Upper side: Leathery. Under side: Smooth.
- *Ribs and veins.*—Ordinary.
- *Edge.*—Serrated.
- *Serration.*—Single.
- *Petiole.*—Rachis: Color—Green. Under side: Prickly.
- *Stipules.*—Short; serrated.

Wood:
- *New wood.*—Color: Light green. Bark: Smooth.
- *Old wood.*—Color: Green. Bark: Smooth.

Thorns:

*Quantity.*—On main stalks from base: Many. On laterals from stalk: Many.

*Form.*—Broad base; slightly hooked downward.

*Color (when young).*—Green, with red shading.

*Position.*—Irregular.

Prickles:

*Quantity.*—On main stalks: Few. On laterals: Few.

*Color.*—Brown.

I claim:

1. A new and distinct variety of rose plant of the floribunda class, substantially as herein shown and described, characterized particularly as to novelty by the unique combination of a vigorous and well-branched plant habit attaining an average height of about 2½ feet, flowers of medium size and which are borne both singly and in small clusters, and a distinctive and attractive Saffron Yellow flower color which is overcast distinctively on the petal tips with Brick Red.

No references cited.

ROBERT E. BAGWILL, Primary Examiner